United States Patent
Axelsson

(10) Patent No.: US 7,452,346 B2
(45) Date of Patent: Nov. 18, 2008

(54) COUPLING DEVICE AND MEDICAL LINE SET INCLUDING SAME

(75) Inventor: Mikael Axelsson, Furulund (SE)

(73) Assignee: Gambro Lundia AB (SE)

( * ) Notice: Subject to any disclaimer, the term of this patent is extended or adjusted under 35 U.S.C. 154(b) by 525 days.

(21) Appl. No.: 10/250,482

(22) PCT Filed: Dec. 19, 2001

(86) PCT No.: PCT/SE01/02813

§ 371 (c)(1),
(2), (4) Date: Nov. 5, 2003

(87) PCT Pub. No.: WO02/053211

PCT Pub. Date: Jul. 11, 2002

(65) Prior Publication Data

US 2004/0067161 A1    Apr. 8, 2004

(30) Foreign Application Priority Data

Jan. 8, 2001  (SE) .................................. 0100043

(51) Int. Cl.
*A61M 1/00* (2006.01)
*A61M 39/10* (2006.01)
*A61M 25/16* (2006.01)

(52) U.S. Cl. .......................... 604/29; 604/533; 604/534

(58) Field of Classification Search ................. 604/533, 604/6.16, 29, 30, 534, 200, 264, 523; 422/44, 422/46

See application file for complete search history.

(56) References Cited

U.S. PATENT DOCUMENTS

| 4,294,250 | A |   | 10/1981 | Dennehey |
| 5,221,267 | A |   | 6/1993  | Folden |
| 5,259,843 | A | * | 11/1993 | Watanabe et al. ........... 604/256 |
| 5,336,173 | A |   | 8/1994  | Folden |
| 5,338,293 | A |   | 8/1994  | Jeppsson et al. |
| 5,423,768 | A | * | 6/1995  | Folden et al. ................ 604/200 |
| 5,722,947 | A | * | 3/1998  | Jeppsson et al. ............... 604/29 |
| 5,836,619 | A |   | 11/1998 | Shemesh et al. |

FOREIGN PATENT DOCUMENTS

| EP | 0 555 927 A1 | 8/1993 |
| EP | 0 488 288 B1 | 5/1996 |
| JP | 59-139269 | 8/1984 |
| JP | 6125990 | 5/1994 |
| JP | 10234849 | 9/1998 |
| WO | WO 81/01654 | 6/1981 |

* cited by examiner

*Primary Examiner*—Nicholas D Lucchesi
*Assistant Examiner*—Victoria P Campbell
(74) *Attorney, Agent, or Firm*—Finnegan, Henderson, Farabow, Garrett & Dunner L.L.P.

(57) ABSTRACT

The present invention refers to a medical line set (10) having a breakable coupling device (90), and to such a coupling device (90). More particularly the present invention refers to an medical dialysis line set (10), such as a peritoneal dialysis (PD) line set, including a liquid introducing portion (20), a liquid distribution portion or PD portion (40) and a drain portion (80), for introducing and extracting dialysis liquid from a patient, the line set particularly including said coupling device (90) for connecting and disconnecting the liquid introducing portion (20) in order to introduce and extract spent medical solution.

4 Claims, 3 Drawing Sheets

COUPLING DEVICE AND MEDICAL LINE SET INCLUDING SAME

TECHNICAL FIELD

The present invention refers generally to the medical field and specifically to the field of dialysis, such as peritoneal dialysis (PD). More particularly the present invention refers to a medical line set and to a breakable coupling device to be used in such a medical line set. The medical line set may be a peritoneal dialysis line set (PD line set), including a liquid introducing portion connectable with medical supply bags for holding medical solutions, a liquid distribution portion (PD portion) and a drain portion for extracting the solutions, the line set particularly including said coupling device for connecting and disconnecting the liquid introducing portion for introducing and extracting spent medical solution.

BACKGROUND OF THE INVENTION

Dialysis is widely used within medical therapy in the treatment of various diseases and disorders. One example is dialysis in the treatment of patients suffering from different stages of acute and chronic renal diseases. These patients are generally treated either by haemodialysis (HD) or peritoneal dialysis (PD). During HD the metabolic waste products are cleared by means of an artificial membrane outside the body, whereas during PD the waste products are cleared by means of a biological membrane, such as the peritoneum or peritoneal membrane. There are both manual and automated modes of PD and to find the right treatment mode for each patient, medical, social and economical aspects have to be considered.

Continuous Ambulatory Peritoneal Dialysis (CAPD) is a frequently used form of PD. It is a manual method where each exchange is taken care of by the patient himself. To increase the efficiency of CAPD and to help the patient with the exchanges, a machine (e.g. a PD cycler) can be used. A PD cycler is a machine that automatically administers all exchanges of PD solutions according to a predetermined schedule. There are different PD applications when using a machine, all summarised with the term APD, Automated Peritoneal Dialysis.

In the different modes of PD, especially in an APD assembly, a connector is often used to detach a multi-divider tubing system of the PD medical assembly, including the empty PD bags from the PD portion, in order to transfer the empty medical supply bags to the drain portion for discharge of spent PD solution during the following treatment. This is to assist the patient in the situation where there is no sink or the like available for discharge of spent PD solution during the treatment.

Presently known is an APD system including a standard luer lock connection having a female connecting part and a male connecting part for connecting the liquid introducing portion to the PD portion. The connection is mounted before sterilisation of the whole assembly. After sterilisation and completion of the dialysis procedure the connection is unscrewed and the liquid introducing portion is connected to the drain portion of the next PD medical assembly.

One major disadvantage with said connection is that the connector tends to get loose during sterilisation as well as during storage and air maybe sucked into or leak into the tubing system of the assembly. Air in the system may cause pain to the patient and may even be fatal. Moreover, a loose-fitting connector provides a potential for bacterial contamination of the line set, which in turn may result in serious inflammation of the peritoneum of the patient.

A further disadvantage with the above construction is, due to the construction of the distinct elements forming the connector ends, that each connector end is required to be manufactured separately, which is time-consuming and increases costs.

SUMMERY OF THE INVENTION

It is towards the need for an improved medical assembly with a safe and simple construction which may be sterilised and stored without the risk of air leakage or bacterial contamination, that the present invention is directed.

Thus, one object of the invention is to provide a medical line set, including a coupling device, which is safe as regards the risk of air leakage or bacterial contamination after sterilisation and during storage.

One further object is to provide an improved coupling device for said medical line set which has a simple construction resulting in a low manufacturing cost.

In order to fulfil the above objects the present invention provides a medical line set having a liquid introducing portion with at least one first connector, a liquid distribution portion with a second connector and a drain portion with a third connector, the line set further comprising a coupling device for connecting the liquid introducing portion to the liquid distribution portion, said coupling device having
  a first connecting part connectable with the liquid distribution portion;
  a central part;
  a second connecting part connectable with the liquid introducing portion, the central part and the second connecting part being integrally formed with the first connecting part; and
  a predetermined breaking section between the central part and the first connecting part.

In one aspect of the invention the medical line set is a PD line set and in a preferred aspect it is an APD line set.

According to the present invention there is also provided a coupling device, which is particularly useful in a medical dialysis line set having a liquid introducing portion with at least one first connector, a liquid distribution portion with a second connector and a drain portion with a third connector for connecting the liquid introducing portion to the liquid distribution portion, said coupling device comprising
  a first connecting part connectable with the liquid distribution portion;
  a central part;
  a second connecting part connectable with the liquid introducing portion, the central part and the second connecting part being integrally formed with the first connecting part; and
  a predetermined breaking section between the central part and the first connecting part.

In a preferred embodiment the central part of the coupling device of said medical line set is adapted to be connectable with the third connector.

In a further preferred embodiment the predetermined breaking section of the coupling device of said medical line set is defined by a groove in the junction between the central part and the first connecting part and is breakable at finger pressure.

In one aspect the coupling device is adapted to be used in a PD line set and in a preferred aspect it is adapted to be used in an APD line set.

Moreover, the present invention provides a method for performing dialysis in a medical line set having a liquid introducing portion with at least one first connector, a liquid distribution portion with a second connector and a drain portion with a third connector, the line set further comprising a coupling device for connecting the liquid introducing portion to the liquid distribution portion.

According to a preferred aspect the method refers to a method of performing dialysis in an PD line set and more preferably in an APD line set.

By means of the present invention the risk for patients on dialysis to be harmed due to air leakage into the system or bacterial contamination thereof is minimised. A further benefit provided by the present invention is that the coupling device is easy to produce and easy to mount, which makes the coupling device, as well as the medical line set including the coupling device, safe and economical. Moreover, by manufacturing the coupling device as an integrated moulded product, the cost of manufacturing the PD tubing set is decreased.

DETAILED DESCRIPTION OF THE INVENTION

The medical line set according to the invention has a liquid introducing portion, a liquid distribution portion, a drain portion and a coupling device for connecting the liquid introducing portion to the liquid distribution portion.

The medical line set of the invention is preferably a medical dialysis line set, such as a PD line set and more particularly an APD line set.

Figure 1:
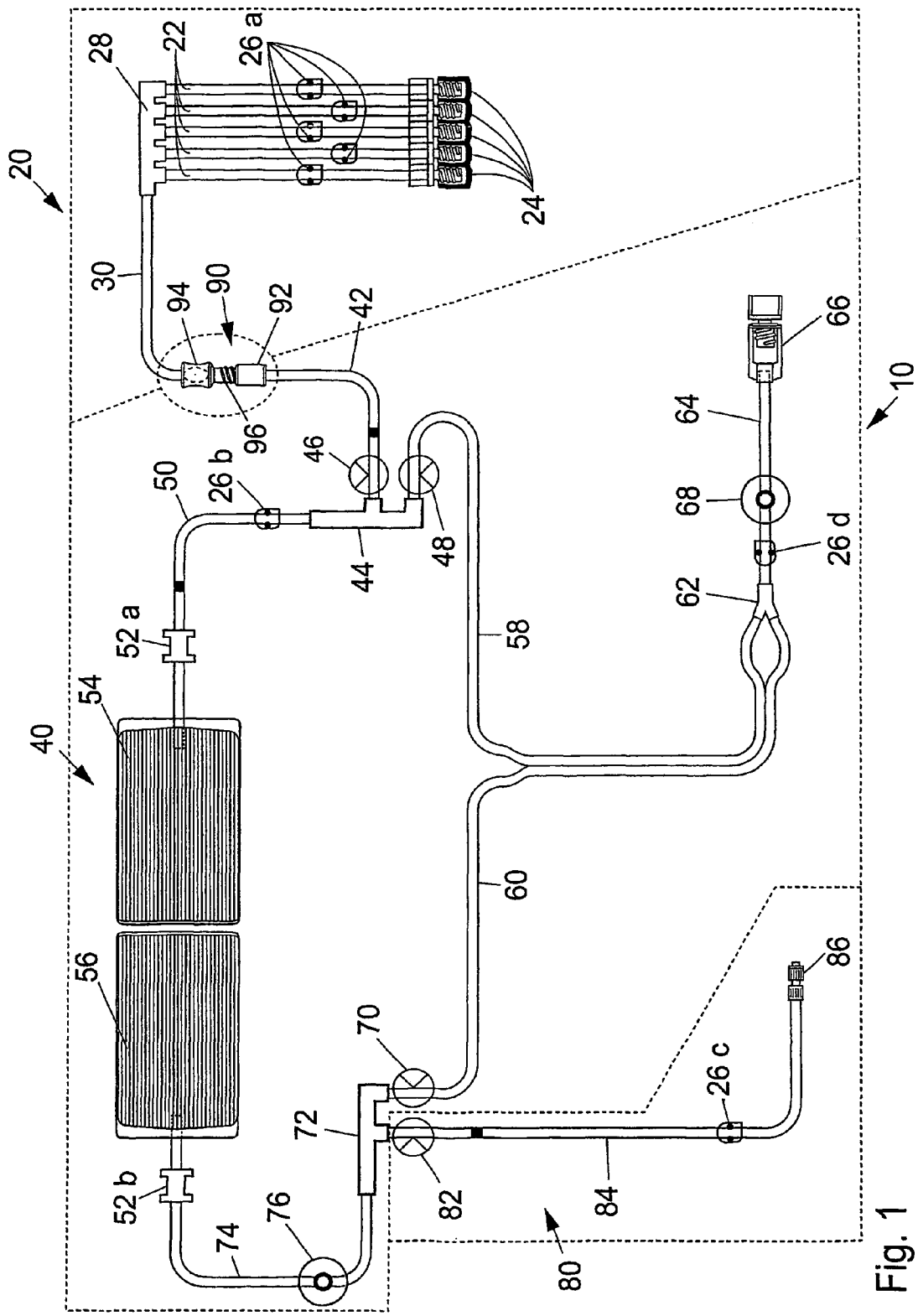
FIG. 1 is a schematic view of a medical line set according to the present invention including a coupling device according to the invention.

Referring to FIG. 1 one embodiment of a medical line set according to the present invention is shown. The medical line set 10 is a medical line set for APD. The APD line set 10 includes a liquid introducing portion 20, a liquid distribution portion or PD portion 40, a drain portion 80 and a coupling device 90. According to the embodiment shown in FIG. 1 the coupling device 90 is placed between the liquid introducing portion 20 and the liquid distribution portion 40. The coupling device 90 has a first connecting part 92, a second connecting part 94 and a central part 96. The first connecting part 92 of the coupling device 90 is connected to the liquid distribution portion 40 and the second connecting part 94 of the coupling device 90 is connected to the liquid introducing portion 20.

The liquid introducing portion 20 includes connection tubes 22 with clamps 26a and one or more first connectors 24 adapted for the introduction of different medical solutions from medical supply bags (not shown). The liquid introducing portion 20 further includes a distributor 28 and a first feed line 30 for delivering the medical solutions to the liquid distribution portion 40.

The liquid distribution portion 40 includes according to the embodiment shown in FIG. 1 a heater bag 54 and a drain bag 56. The heater bag 54 is used for the medical solution, e.g. a PD solution, to be preheated, weighted and introduced into the patient and the drain bag 56 is intended for the spent PD solution being extracted from the patient after the peritoneal dialysis is finished.

In connection with the heater bag 54 there is provided a second feed line 42, a dose valve 46, a first F-connector 44, a third feed line 50 provided with a clamp 26b and a first seal 52a for introducing medical solutions from the liquid introducing portion 20 to the heater bag 54. Liquid from the heater bag 54 flows into a patient via an inflow valve 48, an inflow line 58, a Y-connector 62, a patient line 64 provided with a clamp 26d and an injection port 68, and a second connector 66 attached to a PD catheter (not shown) entered into the peritoneal cavity of the patient.

In connection with the drain bag 56 of the liquid distribution portion 40 there is provided a second seal 52b, a first drain line 74, a second F-connector 72, a sampling port 76 and an outflow line 60 having an outflow valve 70 for allowing liquid to flow, on one hand, from the patient to the drain bag 56 and, on the other hand, from the drain bag 56 to the drain portion 80.

The drain portion 80 of the medical line set 10 includes a second drain line 84, having a drain valve 82 and a clamp 26c, and a third connector 86. Said third connector 86 is adapted to be connectable with the coupling device 90 for discharge of used PD solution.

According to a preferred embodiment the coupling device 90 and the third connector 86 are both standard luer lock or luer cone connectors.

The present invention also refers to a coupling device which may be used in a medical line set as described above.

Figure 2:
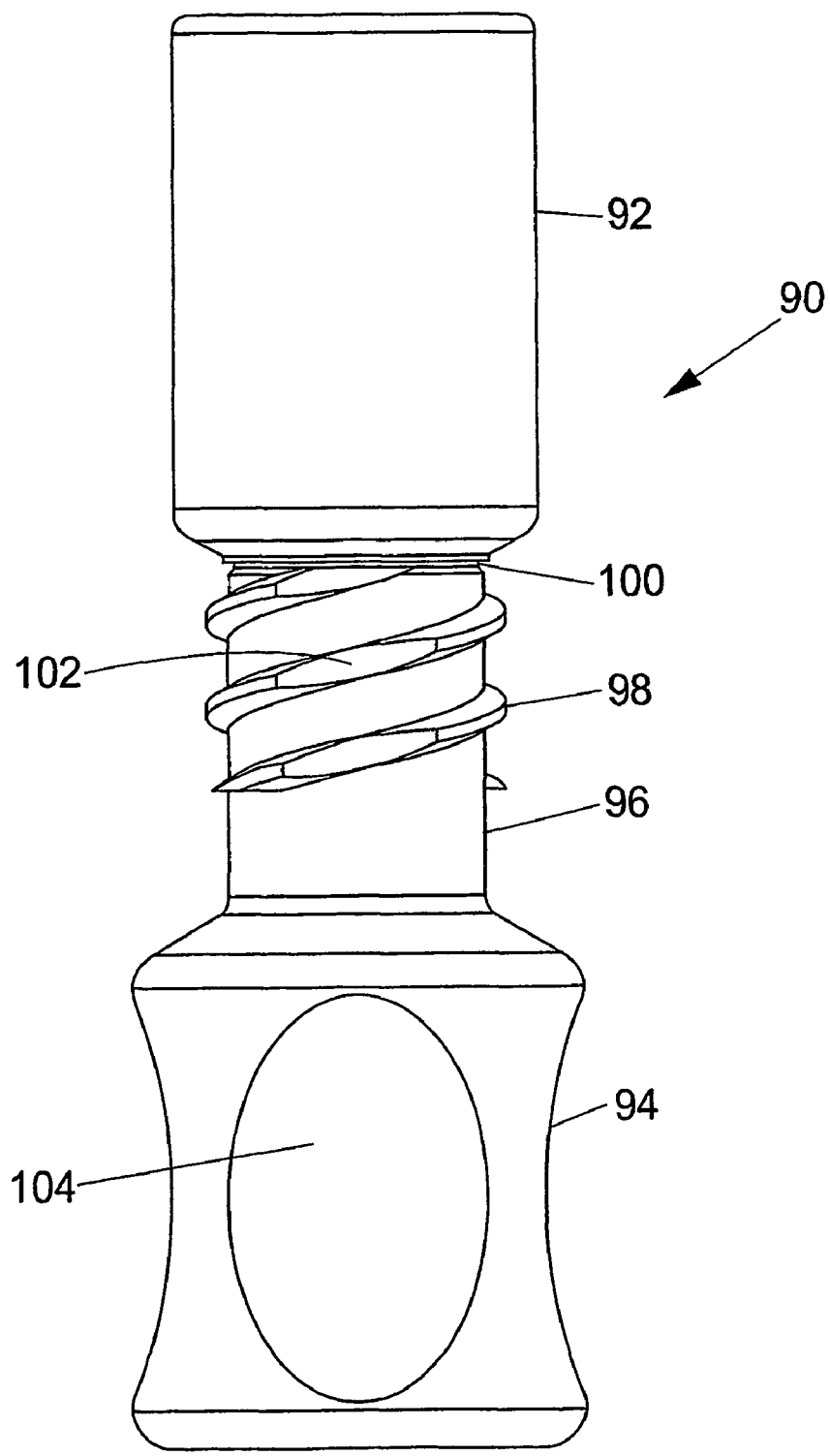
FIG. 2 is a front view of a coupling device according to the present invention.
Figure 3:
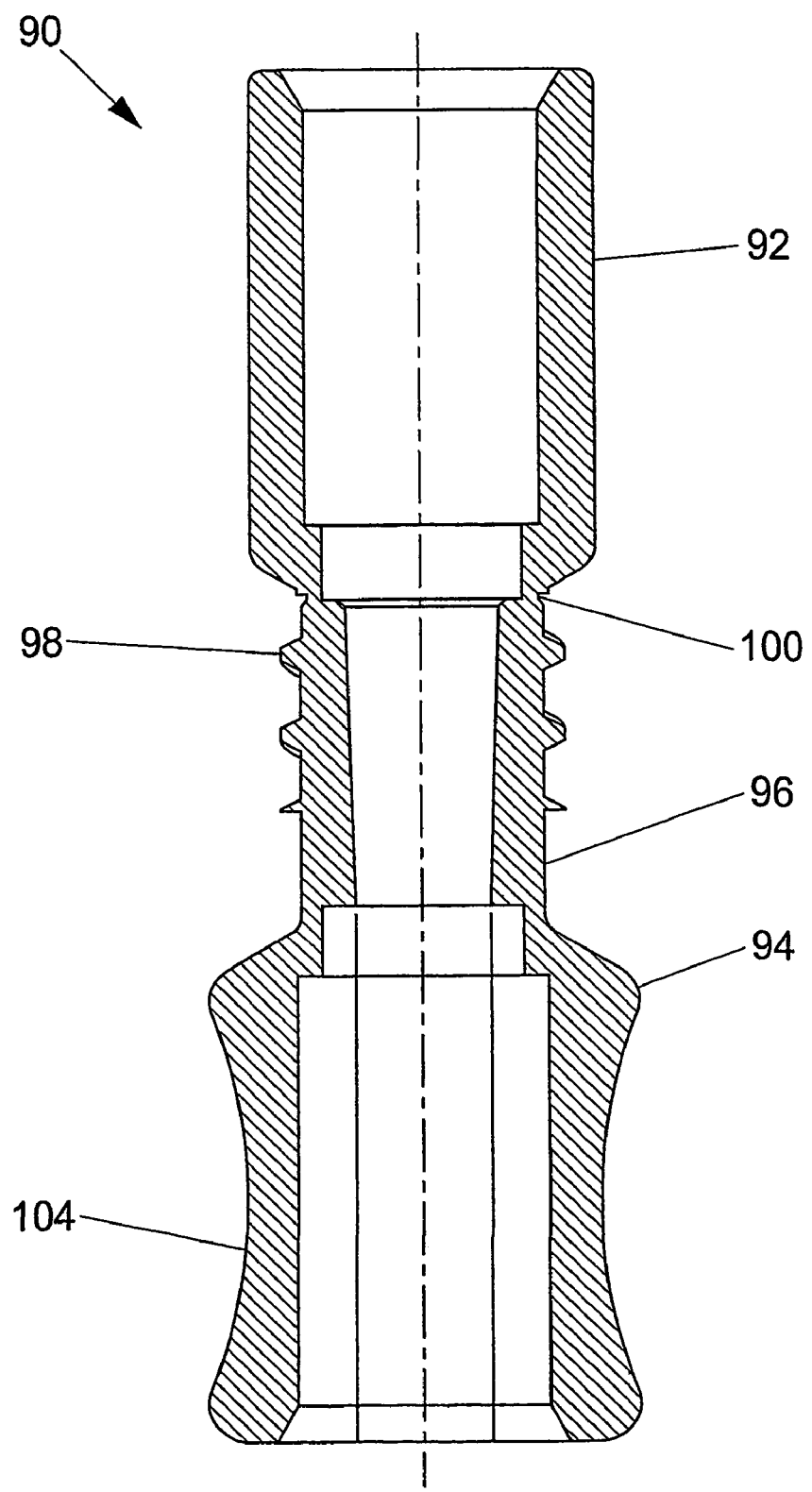
FIG. 3 is a cross sectional view of a coupling device according to the present invention.

Referring now to FIGS. 2 and 3 there is shown one embodiment of a coupling device according to the invention. The coupling device 90 has a first connecting part 92, a central part 96 and a second connecting part 94. These three parts 92, 96 and 94 are all cylindrically shaped tubular parts and are formed in one piece.

The central part 96 is provided with a predetermined breaking section 100 defined by a circumferential groove in the junction between the central part 96 and the first connecting part 92. The coupling device 90 is adapted to be broken along this predetermined breaking section 100 into two pieces. The thickness of the material of the breaking section 100 is such that the breaking section 100 may be broken when either of the first connecting part 92 and the second connecting part 94 is twisted or bent. The breaking section 100 is breakable at finger pressure.

Furthermore, the central part 96 of the coupling device 90 is preferably provided with threads 98 along the whole or part of its length. With reference to FIG. 2 a coupling device 90 is shown wherein the central part 96 is provided with threads 98 along part of its length, i.e. the part close to the breaking section. In order to facilitate the manufacturing of the coupling device 90 as an integral piece the threads 98 of the central part may, as shown in FIG. 2, be divided into two parts along the circumference of the central part 96. As appears from FIG. 2 part of the threads may be bevelled resulting in bevelled surfaces 102. Alternatively, the threads may be distinctly divided into two or more groups.

In the embodiment shown in FIGS. 2 and 3, the central part 96 is shaped in the form of a male luer cone having standard luer cone dimensions. Said standard dimensions of a male luer cone connector is as follows: the connection diameter is 4.29 mm and the length of the cone is at least 7.5 mm with a cone angle of 1°43'6" towards the smallest diameter of the luer cone. The connection diameter of the luer cone is, with reference to FIG. 2, the diameter adjacent the first connecting part 92 at the predetermined breaking section 100 and the smallest diameter of the luer cone is the one adjacent the second connecting part 94.

The second connecting part 94 is preferably provided with two or more gripping surfaces 104 for twisting said second connecting part 94 around its axis with the fingers in order to separate the second connecting part 94 and the central part 96 from the first connecting part 92. The second connecting part 94 of the coupling device 90 shown in FIG. 2 is provided with four gripping surfaces regularly arranged around said second connecting part 94. While any number of gripping surfaces may be provided, the number is suitably at least two.

Preferably the coupling device has the form of a luer lock connector, the central part thereof having the form of a male luer cone.

According to another embodiment the luer cone luer lock connector may be presented without threads, the central part having the form of a male luer cone adapted to be pressed into a mating female luer connector.

Moreover, the present coupling device may have any suitable dimensions as long as it is adapted to be coupled to a mating connector, shown as the third connector 86 in FIG. 1. The central part 96 may e.g. vary in length.

Breaking the present coupling device 90 along the predetermined breaking section 100 results in two pieces, one piece comprising the threaded part or the cone formed part to be the drain portion, i.e. the central part 96 and the second connecting part 94, and connected to the other piece comprising the first connecting part 92.

The coupling device of the present invention is produced in one piece through any suitable known technique, such as injection moulding and form pressing. The coupling device may be made of any suitable material, e.g. thermoplastic polymers, such as polyvinyl chloride, polystyrene and polyurethane, or combinations thereof.

According to a preferred embodiment the coupling device according to the invention is made of polyvinyl chloride by injection moulding under standard process conditions well known within the art.

The method for performing dialysis in a dialysis line set according to the present invention is described with reference to FIG. 1. It implies the use of a medical line set 10 having a liquid introducing portion 20 with at least one first connector 24, a liquid distribution portion or PD portion 40 with a heater bag 54, a drain bag 56 and a second connector 66, and a drain portion 80 with a third connector 86, the line set further comprising a coupling device 90 having a first connecting part 92 connectable with the liquid distribution portion 40; a central part 96 adapted to be connected with the third connector 86; a second connecting part 94 connectable with the liquid introducing portion 20, the central part 96 and the second connecting part 94 being integrally formed with the first connecting part 92; and a predetermined breaking section 100 defined by a groove in the junction between the central part 96 and the first connecting part 92 and being breakable at finger pressure. Said method comprises the steps of introducing a PD solution via the liquid introducing portion 20 into the heater bag 54 to prepare a predetermined dose of the PD solution;

introducing said dose of PD solution into the peritoneal cavity of a patient;

allowing the predetermined dose of PD solution to reside in the peritoneal cavity of the patient for a predetermined dwell period;

extracting the used PD solution from peritoneal cavity of the patient and allowing said used solution to enter the drain bag 56;

separating the liquid introducing portion 20 from the liquid distribution portion 40 through breaking the predetermined breaking section 100, thus separating the central part 96 and the second connecting part 94 of the coupling device from the first connecting part 92; and connecting the central part 96 and the second connecting part 94 to the third connector 86 of the drain portion 80 for draining the used PD solution via the drain portion 80 to the medical supply bags (not shown).

The coupling device and the medical line set of the invention is preferably used in an APD system, but may also be used in other systems, having the need for a coupling device according to the invention.

The function of a medical line set according to the invention will now be described with reference to the embodiment shown in FIG. 1, wherein the medical line set is an APD medical line set.

First a sterile medical line set 10 is mounted on a PD cycler (not shown). The PD cycler includes four valves, dose valve 46, inflow valve 48, outflow valve 70 and drain valve 82, which are all initially closed. The liquid flow on the PD cycler can be created optional, by e.g. gravitation, in a pressure chamber, with a pump etc. Clamps 26*a, b, c, d* of the PD medical line set 10 shall now be closed. The first connectors 24, which maybe screw connectors, piercing connectors etc., are attached to medical supply bags (not shown) including for the treatment required solutions. The liquid introducing portion of a medical PD line set used in a previous treatment (not shown) is attached to the third connector 86 of the drain portion 80. Now the clamps 26*a* are opened and the PD medical line set is automatically primed with PD solution. The dose valve 46 of the PD cycler and clamp 26*b* are opened and liquid from the medical supply bags flows through first and second feed lines 30 and 42 via the first F-connector 44 and the third feed line 50 to the heater bag 54 to prepare a required and predetermined dose of a PD solution. When the required dose has been filled into the heater bag 54 the dose valve 46 is closed. In the meantime the second connector 66 is connected to a PD catheter (not shown) of a patient to be treated. The PD solution in the heater bag 54 is heated to around body temperature and weighed a first time to define a first weight. The inflow valve 48 and the clamp 26*d* are opened and the PD solution is allowed to flow through the inflow line 58 and the patient line 64 into the peritoneal cavity of the patient via the second connector 66 and the PD catheter of the patient. When the required dose of PD solution has been distributed to the patient the inflow valve 48 is closed. The injection port 68 on the patient line 64 may be used for injecting into the patient any further solution, substance, etc. such as insulin and antibiotics. Alternatively, it may be used for taking samples, such as samples of the spent PD solution.

After a predetermined dwell period, i.e. the time during which the PD solution is residing in the peritoneal cavity without being administered or drained and during which time the dialysis exchange is taking place, the outflow valve 70 is opened and the spent PD solution is allowed to enter the drain bag 56 through patient line 64, outflow line 60, second F-connector 72 and first drain line 74. The outflow valve 70 is closed, the spent PD solution, now in the drain bag 56, is weighed a second time to define a second weight. Said second weight is compared to the first weight of the heater bag 54 and the difference between the two weights is calculated for monitoring and controlling the treatment. The sampling port 76 may be used for taking samples of the spent PD solution.

Finally, the drain valve 82 and the clamp 26*c* are opened and the spent and weighed PD solution is drained through the second drain line 84 into the empty medical supply bags used in a previous treatment and attached via the third connector 86. After completion of a treatment the liquid introduction portion 20 of the medical PD line set used in the previous treatment is disconnected from the third connector 86 of the drain portion 80 and discarded. In this final step the coupling device 90 of the now used medical line set (10) is separated into two pieces, one piece comprising the first connecting part 92 and the other piece comprising the second connecting part 94 and the central part 96, by breaking the predetermined breaking section 100 through twisting or bending either of the connecting parts. The resulting second connecting part 94 together with the central part 96 having the shape of a luer lock is then connected to the mating third connector 86, which has the form of a mating luer lock. In general the patient does not separate the coupling device into two pieces, thus moving the liquid introducing portion to the drain portion, until just before the next treatment.

The medical line set including the coupling device according to the invention may, if needed and suitable, include two or more of said coupling devices.

One example of liquid used in the medical line set according to the invention is a PD solution and it may be any PD solution known in the art.

The integrally formed coupling device of the invention is easy, safe and economic to manufacture. Moreover, mounting of the coupling device is easy and safe. Being formed in one piece the coupling device is safe from air-leakage and bacterial contamination after sterilisation and during storage.

A preferred embodiment of the invention has been described. However, many variations of the invention, which are within the spirit and scope of the invention as claimed in the following claims, may be made.

| Reference numerals: | |
|---|---|
| 10 | medical line set |
| 20 | liquid introducing portion |
| 22 | connection tube |
| 24 | first connector |
| 26a, b, c, d | clamp |
| 28 | distributor |
| 30 | feed line, first |
| 40 | liquid distribution portion/PD portion |
| 42 | second feed line |
| 44 | first F-connector |
| 46 | dose valve |
| 48 | inflow valve |
| 50 | third feed line |
| 52a, b | seal |
| 54 | heater bag |
| 56 | drain bag |
| 58 | inflow line |
| 60 | outflow line |
| 62 | Y-connector |
| 64 | patient line |
| 66 | second connector |
| 68 | Injection port |
| 70 | outflow valve |
| 72 | second F-connector |
| 74 | first drain line |
| 76 | sampling port |
| 80 | drain portion |
| 82 | drain valve |
| 84 | second drain line |
| 86 | third connector |

| -continued | |
|---|---|
| Reference numerals: | |
| 90 | coupling device |
| 92 | first connecting part |
| 94 | second connecting part |
| 96 | central part |
| 98 | thread |
| 100 | predetermined breaking section |
| 102 | bevelled surface |
| 104 | gripping surface |

The invention claimed is:

1. A method for performing peritoneal dialysis with a medical line set having a liquid introducing portion with at least one first connector, a liquid distribution portion or PD portion with a second connector, and a drain portion with a third connector, the line set further comprising a coupling device for connecting the liquid introducing portion to the liquid distribution portion, said coupling device having:
   a first connecting part connectable with the liquid distribution portion;
   a central part;
   a second connecting part connectable with the liquid introducing portion, the central part and the second connecting part being integrally formed with the first connecting part;
   and a predetermined breaking section between the central part and the first connecting part, the method comprising the steps of:
   introducing a medical solution via the liquid introducing portion into a heater bag to prepare a predetermined dose of a peritoneal dialysis (PD) solution;
   introducing said predetermined dose of PD solution into the peritoneal cavity of a patient;
   allowing the predetermined dose of PD solution to reside in the peritoneal cavity of the patient for a predetermined dwell period;
   extracting the used PD solution from peritoneal cavity of the patient and allowing said used solution to enter the drain bag;
   separating the liquid introducing portion from the liquid distribution portion through breaking the predetermined breaking section, thus separating the central part and the second connecting part of the coupling device from the first connecting part; and
   connecting the central part and the second connecting part to the third connector of the drain portion for draining the used PD solution via the drain portion.

2. The method according to claim 1, wherein the line set is a peritoneal dialysis line set.

3. The method according to claim 2, wherein the line set is an automated peritoneal dialysis line set.

4. The method according to any one of claims 1-3, wherein the central part of the coupling device has the shape of a luer lock connector.

* * * * *